United States Patent [19]

Barbera

[11] Patent Number: 5,219,570
[45] Date of Patent: Jun. 15, 1993

[54] AGGLOMERATED PSYLLIUM HUSK CONTAINING EDIBLE ACID

[75] Inventor: Melvin A. Barbera, Cincinnati, Ohio

[73] Assignee: The Procter & Gamble Company, Cincinnati, Ohio

[21] Appl. No.: 858,448

[22] Filed: Mar. 25, 1992

Related U.S. Application Data

[63] Continuation of Ser. No. 391,915, Aug. 10, 1989, abandoned.

[51] Int. Cl.$^5$ ................ A61K 35/78; A61K 31/70
[52] U.S. Cl. .................... 424/195.1; 514/48; 514/892; 514/937
[58] Field of Search ............. 424/195.1, 440; 514/58, 514/892, 937

[56] References Cited

U.S. PATENT DOCUMENTS

| | | | |
|---|---|---|---|
| 4,459,280 | 7/1984 | Colliopoulos et al. | 424/440 |
| 4,548,806 | 10/1985 | Colliopoulos et al. | 424/440 |
| 4,551,331 | 11/1985 | Rudin | 424/195.1 |
| 4,828,842 | 5/1989 | Furst et al. | 424/195.1 |

*Primary Examiner*—John W. Rollins
*Attorney, Agent, or Firm*—Kim William Zerby; Douglas C. Mohl; Jack D. Schaeffer

[57] ABSTRACT

Agglomerated psyllium husk comprising edible acid uniformly dispersed throughout the agglomerating coating. Preferred are maltodextrin-containing agglomerates of psyllium husk comprising citric acid uniformly dispersed throughout the maltodextrin coating. This agglomerated psyllium husk has improved mixability and dispersibility in liquids.

6 Claims, No Drawings

AGGLOMERATED PSYLLIUM HUSK CONTAINING EDIBLE ACID

This is a continuation of application Ser. No. 07/391,915 filed Aug. 10, 1989, now abandoned.

BACKGROUND OF THE INVENTION

The present invention relates to agglomerated psyllium husk comprising edible acid (e.g., citric acid) uniformly dispersed throughout the agglomerating coating. This modification to agglomerated psyllium husk improves the mixability and dispersibility of the psyllium husk in a liquid. The present invention also relates to processes for manufacturing the agglomerated psyllium husk of the present invention.

Products containing psyllium seed husk are known (e.g., Metamucil®, sold by The Procter & Gamble Company). Such products are useful for the benefit of normalizing bowel function and laxation. In addition, recent research has demonstrated the effectiveness of psyllium seed husk fiber in reducing human serum cholesterol levels and in controlling blood glucose levels in diabetics.

Psyllium seed husk contains natural mucilage. It forms a gelatinous mass on contact with water, and it exhibits poor dispersibility and mixability in water. The psyllium husk particles tend to agglomerate when mixed with water. Hydration takes place over the surface of such agglomerated aggregates to form gel-coated lumps, the interiors of which are still substantially dry. These lumps are extremely difficult to disperse.

One way of reducing these problems while improving the taste of the psyllium product has been to use high percentages of sugar in the drink mix. The dispersibility and mixability are improved, but diabetics and people on reduced calorie diets may have difficulty taking such products in view of the high sugar content.

U.S. Pat. No. 4,321,263, to Powell et al., issued Mar. 23, 1982, discloses a method of improving the dispersibility of psyllium powder. It is described therein to wet the psyllium particles with an alcoholic solution of at least one of polyethylene glycol and polyvinylpyrrolidone and granulating the thus-coated particles.

U.S. Pat. No. 4,551,331, to Rudin, issued Nov. 5, 1985, describes a modified dry dietary fiber product which is said to be readily dispersible in liquids. The dry dietary fiber product (e.g., psyllium) comprises a coating of from 0.05 to 20% of a food grade emulsifier. The processes for making such products are said to comprise blending the dietary fiber product materials with the mixture of a non-toxic solvent in a food grade emulsifier followed by removing the solvent. Examples 5 and 6 illustrate aspartame-containing compositions to be dispersed in water which contain citric acid and coated psyllium.

U.S. Pat. No. 4,459,280, to Colliopoulos et al., issued Jul. 10, 1984, and U.S. Pat. No. 4,548,806, to Colliopoulos et al., issued Oct. 22, 1985, described improving mixability and dispersibility of psyllium mucilloid by applying a film of hydrolyzed starch oligosaccharide, a mono- or di-saccharide, a polyglucose, or a polymaltose to the psyllium. Preferred therein is agglomerating the psyllium mucilloid. One suitable polyglucose described therein is polydextrose, said to be "a partially metabolizable, water-soluble polymer prepared by the condensation of a melt which consists of approximately about 89% D-glucose, about 10% sorbitol and about 1% citric acid on a weight basis."

Thus, while there has already been much research devoted to improving the dispersibility of psyllium fiber in liquids, there continues to be a need for improved products and processes for obtaining readily dispersible psyllium fiber. It has been surprisingly discovered that uniformly dispersing an edible acid throughout the agglomerating coating applied to psyllium husk improves mixability, dispersibility, and product aesthetics, as well as in some cases storage stability, for psyllium husk products having low (less than about 20%) sugar content.

It is therefore an object of the present invention to provide improved agglomerated psyllium husk comprising an agglomerating coating throughout which is uniformly dispersed an edible acid. It is a further object to provide agglomerated psyllium husk having improved mixability and dispersibility in a liquid, especially water. A further object is to provide such agglomerated psyllium husk having good aesthetics and easy preparation as drinks. An object is also to provide low calorie agglomerated psyllium husk, and low calorie psyllium-containing drink mixes, having low (less than about 20%) sugar content. Additionally, an object is to provide agglomerated psyllium-containing products having improved storage stability. Finally, an object is to provide processes for producing agglomerated psyllium husk and psyllium-containing drink mixes.

These and other objects of the present invention will become readily apparent from the detailed description which follows.

All percentages and ratios used herein are by weight unless otherwise specified. Screen mesh sizes used herein are based on U.S. standards.

SUMMARY OF THE INVENTION

The present invention relates to agglomerated psyllium husk. Said agglomerated psyllium husk comprises: (a) from about 25% to about 99% psyllium husk; (b) from about 0.5% to about 20% of agglomerating material coating on said psyllium husk; and (c) from about 0.5% to about 20% of edible acid uniformly dispersed throughout the agglomerating material coating on said psyllium husk, and wherein further said agglomerated psyllium husk comprises less than about 20% sugar.

The present invention further relates to processes for producing agglomerated psyllium husk according to the present invention. Said processes comprise the steps of: (a) coating to agglomerate a psyllium-containing blend with a solution mixture comprising one or more agglomerating materials and one or more edible acids; (b) drying the agglomerated psyllium husk; and (c) optionally, repeating steps (a) and (b), but at least as many times as necessary to have said agglomerated psyllium husk comprise at least about 0.5% of said edible acid uniformly dispersed throughout the agglomerating material coating on said psyllium husk.

DETAILED DESCRIPTION OF THE INVENTION

It has been surprisingly discovered that the mixability and dispersibility, as well as aesthetics and/or storage stability, of agglomerated psyllium husk is improved when edible acid is dispersed uniformly throughout the agglomerating material coating on psyllium husk. Benefits of the same type and/or degree are not observed when none of the edible acid is uniformly dispersed throughout the agglomerating material coating (e.g., as occurs when the edible acid is simply dry blended with agglomerated psyllium husk).

The psyllium husk used in the present invention is from psyllium seeds, from plants of the Plantago genus. Various species such as *Plantago lanceolate*, *P. rugelii*, and *P. major* are known. Commercial psyllium husk include the French (black; *Plantago indica*), Spanish (*P. psyllium*) and Indian (blonde; *P. ovata*). Indian (blonde) psyllium husk is preferred for use herein. Also preferred is psyllium husk which is at least about 85% pure, more preferably at least about 90% pure, and most preferably at least about 95% pure. Compositions of the present invention comprise from about 25% to about 99% psyllium husk, preferably from about 50% to about 98%, and more preferably from about 50% to about 90%.

The psyllium husk is obtained from the seed coat of the psyllium seeds. It is typical to remove the seed coat from the rest of the seed by, for example, slight mechanical pressure, and then to use only the seed coat. The seed coat is preferably removed and sanitized by methods known in the art. Preferred is sanitized psyllium seed husk having substantially intact cell structure, the sanitization having been accomplished by methods such as ethylene oxide sanitization and superheated steam sanitization (as taught in European Patent Application Publication No. 308,003, published Mar. 22, 1989 by The Procter & Gamble Company, the disclosures of which are incorporated herein by reference in their entirety). It is also preferred that the psyllium husk used herein have reduced particle size. Preferably the particle size of the psyllium husk is such that more than about 90% of the psyllium husk passes through about 40 mesh screen, and more preferably such that essentially all passes through about 80 mesh screen.

The agglomerating materials useful herein are known, having been described in detail in U.S. Pat. No. 4,548,806 and U.S. Pat. No. 4,459,280, both to Colliopoulos et al., the disclosures of which are incorporated herein by reference in their entirety. These agglomerating materials are selected from the group consisting of water dispersible hydrolyzed starch oligosaccharide, monosaccharide, di-saccharide, polyglucose, polymaltose, and mixtures thereof. Compositions of the present invention comprise from about 0.5% to about 20% of agglomerating material coating on said psyllium husk, preferably from about 1% to about 10%, and more preferably from about 1% to about 5%.

Starches consist of granules separated from edible sources such as potato, arrowroot, oats, wheat, peas, beans, rice, corn, buckwheat, tapioca, rye or barley. A preferred source of starch is corn. The granules exist as a polymeric compound consisting of about 27% linear polymer (amylose) and 73% branched polymer (amylopectin), with these two polymers so associated in the crystal lattice that they are practically insoluble in cold water or alcohol. Starch is soluble in boiling water giving a colloidal solution which may form a jelly on cooling.

Hydrolysis of starch may be accomplished by a reaction of either acid, enzymes (e.g., alpha-amylase, beta-amylase or amyloglucosidase), or a combination of the two either together or reacted in series. The hydrolysis will follow different pathway depending on whether acids or enzymes are used. The result is a mixture of oligosaccharides which may be separated for their different properties. The resulting separated water dispersible (preferably soluble) hydrolyzed starch oligosaccharides are classified by their reducing sugar content, i.e., the mono- or di-saccharides such as glucose or fructose. The percent reducing sugar content in the particular hydrolyzed starch oligosaccharide is measured on a weight/weight basis as the Dextrose Equivalent (or "D.E."). Hydrolyzed starch oligosaccharides with a D.E. of from 0 to 20 are called maltodextrins. The solid maltodextrins have low to moderate sweetness, low to moderate hygroscopicity, solubility in water and alcohol, and have reduced browning. Above a D.E. of about 20 the hydrolyzed starch oligosaccharides are called syrup solids. The syrup solids are soluble but have a more noticeable sweetness and are more hygroscopic. Above a D.E. of about 30, the syrup solids become less desirable for use herein. A preferred water dispersible hydrolyzed starch oligosaccharide therefore has a D.E. of from about 0 to about 30. A preferred maltodextrin has a D.E. of from about 5 to about 20, more preferably about 10 (i.e., a reducing sugar content ratio of 10% w/w of the oligosaccharide).

The mono-saccharides are those carbohydrates that in general are aldehyde-alcohols or ketone alcohols that are a hexose or pentose and have a sweet taste. They are readily soluble in water and form crystalline solids. Examples of the mono-saccharides are dextrose, mannose and fructose. The di-saccharides are those carbohydrates which yield two mono-saccharides on hydrolysis. Examples of di-saccharides are lactose, sucrose and maltose.

Polyglucose and polymaltose are those compounds exemplified by U.S. Pat. Nos. 3,766,165 and 3,876,794, incorporated herein by reference in their entirety. A commercially available preparation of a polyglucose is called polydextrose and has a low calorie content (1 Kcal/gram) and little or no sweetness. It is primarily used as a low calorie, bulk replacement for sugar in foodstuffs. Polydextrose is a partially metabolizable, water-soluble polymer prepared by the condensation of a melt which consists of approximately 89% D-glucose, about 10% sorbitol and about 1% citric acid on a weight basis.

The term "edible acids", as used herein, means any water soluble acid material having a $pK_a$ of less than about 5 and is safe for ingestion by humans. Examples of edible acids include, but are not limited to, citric acid, ascorbic acid, malic acid, succinic acid, tartaric acid, phosphoric acid, mono-potassium phosphate, and mixtures thereof. Preferred are ascorbic acid and citric acid, with citric acid being most preferred. The agglomerated psyllium husk of the present invention comprises from about 0.5% to about 20% edible acid, preferably from about 1% to about 10%, and more preferably from about 1% to about 5%, uniformly dispersed throughout the agglomerating material coating on the psyllium husk.

It is to be noted that for purposes of the present invention, not all of the edible acid must be uniformly dispersed throughout the agglomerating material coating on the psyllium husk. However, it is necessary that at least about 0.5% edible acid is so uniformly dispersed. The term "uniformly dispersed", as used herein, means that the edible acid is essentially dissolved in the coating, rather than being present as discrete masses of edible acid mixed with the agglomerated psyllium or stuck fast as discrete masses by the coating to the psyllium. Furthermore, while it is preferred that at least 0.5% edible acid be uniformly dispersed throughout all the coating, it is also acceptable to have this edible acid uniformly dispersed throughout only part of the coating, e.g., as might occur if several thin layers of coating were applied (e.g., by alternating spraying and drying) and the edible acid was uniformly dispersed in one or a few, but not all, of these layers.

In addition, the agglomerated psyllium husk prepared according to the present invention (and low calorie psyllium-containing drink mixes comprising this husk) comprises less than about 20% sugar. This is important not only to provide the preferred reduced calorie agglomerated psyllium husk and drink mixes, but also because drink mixes comprising psyllium husk having levels of sugar higher than about 20% are expected to be sufficiently mixable and dispersible in a liquid so that the addition of an edible acid to the coating on the psyllium husk would provide little noticeable benefit to the mixability of such compositions (although some small benefit may even be observed for products having sugar in the range of about 30 to 50%). The term "sugar", as used herein, means mono-saccharides and di-saccharides as described hereinbefore as suitable agglomerating materials, whether or not such materials are coated on the psyllium husk or are otherwise present in the compositions.

The processes of the present invention comprise the steps of (a) coating to agglomerate a psyllium-containing blend, preferably a dry blend, with a solution mixture comprising one or more agglomerating materials (as described hereinbefore) and one or more edible acids (also as described hereinbefore); (b) drying the agglomerated psyllium husk; and (c) optionally, repeating steps (a) and (b). The repeating of steps (a) and (b) indicated in step (c) is only optional, however, if one coating and drying step is sufficient to uniformly disperse at least about 0.5% of the edible acid throughout the agglomerating material coating on the psyllium husk, otherwise it is necessary to repeat steps (a) and (b) at least as many times as necessary to attain at least this level of edible acid uniformly dispersed. Agglomeration techniques are described in the hereinbefore referenced U.S. patents, but preferred is multiple layer coating of the psyllium husk using techniques which result in agglomerating the psyllium husk, e.g., as described in detail in U.S. Pat. Nos. 4,459,280 and 4,548,806, to Colliopoulos et al., incorporated by reference herein; and especially preferred is single layer coating of the psyllium husk in a single pass apparatus whereby an agglomerating material (especially maltodextrin) is applied as a single coating such that from about 5% to about 20% of water is applied to the psyllium husk during the coating process.

Multiple layer coating of the psyllium husk is accomplished, for example, by using fluid bed agglomerating equipment. An example of such fluid bed agglomerating equipment is the Fluid Air, Inc., Model 0300 Granulator-Dryer. Preferred single layer coating of the psyllium husk is achieved by utilizing equipment (referred to herein as single pass fluidizing powder wetting apparatus) which operates preferably by dropping a dry blend psyllium-containing material through a highly turbulent annular zone formed by a cylindrical wall and a rotating shaft with variously pitched attached blades. An agglomerating material-containing solution is sprayed into this zone to contact the dry psyllium-containing blend. The resulting coated and agglomerated psyllium husk is dropped to a fluid bed dryer where the added solvent is removed. An example of this equipment is the Bepex Turboflex Model No. TFX-4 (sold by Bepex Corporation; Minneapolis, Minn. with a six square foot bed vibrating fluid bed dryer (sold by Witte Corporation, Inc.; Washington, N. J.).

The psyllium-containing blend preferably comprises from about 25% to about 100% of psyllium. Optional components for the psyllium-containing blend include, but are not limited to, flavoring agents, sweetening agents (preferably low calorie sweetening agents), coloring agents, agglomerating materials (especially maltodextrin) and/or pharmaceutical agents. As noted hereinbefore, it is preferred that the psyllium-containing blend be dry, but it is possible to utilize suitable solvents (e.g., alcohols and/or water) if one is careful, especially if water is utilized, not to cause substantial hydration and swelling of the psyllium, since this is expected to adversely affect the rate at which psyllium husk can interact with water or other fluids.

The solution mixture comprising one or more agglomerating materials and one or more edible acids will be prepared by selecting a liquid (e.g., alcohol and/or water) as appropriate for the agglomerating materials and edible acids being coated onto the psyllium husk. However, it is preferred that water be utilized. Preferred is also spraying the solution mixture onto a dry psyllium-containing blend. Preferably, when a spraying technique is used, the solution mixture is an aqueous solution comprising from about 5% to about 60% (preferably from about 5% to about 45%; more preferably from about 10% to about 30%) of agglomerating material and from about 0.5% to about 50% (preferably from about 5% to about 30%) of edible acid. It is further preferred that, when maltodextrin is utilized as the agglomerating material and citric acid is utilized as the edible acid, the ratio of maltodextrin to citric acid is within the range of from about 1:10 to about 10:1, preferably from about 1:5 to about 5:1. It is also optionally possible to repeat the coating and drying steps of the present process, thereby building up a coating on the psyllium husk which comprises several thin layers of the agglomerating material/edible acid. In addition, other optional materials may be present in the solution mixture, such as sweetening agents (preferably low calorie sweetening agents), flavoring agents, coloring agents, pharmaceutical agents, and mixtures thereof.

While it is desirable to prepare the agglomerated psyllium husk according to the present invention such that the product collected after the coating is completed is ready for ingestion by mixing it in a liquid, it is also possible to add additional materials (e.g., sweetening agents; flavoring agents; coloring agents; agglomerating materials; edible acids; pharmaceutical agents; mixtures thereof) to the agglomerated psyllium husk to provide the psyllium-containing drink mix product. Typically these additional materials (e.g., in amounts from about 0.01% to about 75%) would be added by dry blending or mixing with the agglomerated psyllium husk (e.g., from about 25% to about 99.99%), but any method which does not substantially adversely affect the mixability of the agglomerated psyllium husk may be used. Furthermore, optionally, it is preferred that agglomerates of psyllium husk having particle size less than about 80 mesh screen be milled such that essentially all of the agglomerates are smaller than about 40 mesh screen, and from about 10% to about 40% of the agglomerates are smaller than about 120 mesh screen.

As noted hereinbefore, the compositions of the present invention optionally comprise agents which may be added as a part of the coating and/or as a part of the psyllium-containing blend and/or added to the agglomerated psyllium husk. Preferred is low calorie sweetening agents including, but not limited to, aspartame, saccharine, cyclamate, acesulfame, and mixtures thereof. Another preferred optional component is flavoring agents. Especially preferred are those flavoring agents which are compatible with the edible acid chosen for the coating of the psyllium husk. Additional optional components are pharmaceutical agents such as, for example, aspirin, non-steroidal anti-inflammatory agents, sennosides, etc.

The following examples further describe and demonstrate embodiments within the scope of the present invention. These examples are given solely for the purpose of illustration and are not to be construed as limitations of the present invention, as many variations thereof are possible without departing from the spirit and scope.

EXAMPLE I

A psyllium-containing dry blend (85.42 parts by weight) comprising 62.96 parts by weight superheated steam sanitized psyllium husks (particle size of 98% minimum through 100 mesh screen) and 22.46 parts by weight Maltrin M100 (maltodextrin having a D.E. of about 10; sold by Grain Processing Corporation; Muscatine, Iowa) is agglomerated by spraying the dry blend with a maltodextrin-containing solution (13.65 parts by weight) comprising 1.82 parts by weight Maltrin M100, 3.64 parts by weight citric acid, and 8.19 parts by weight water using a Bepex Turboflex Model No. TFX-4 (sold by Bepex Corporation; Minneapolis, Minn.) and then drying using a six square foot bed vibrating fluid bed dryer (sold by Witte Corporation, Inc.; Washington, N.J.). By weight of the dried agglomerates thus produced, this process applies 9.0% water to the dry psyllium-containing blend, and the dried agglomerates have 2.0% of a maltodextrin single layer coating and 4.0% of citric acid uniformly dispersed in this maltodextrin coating. The agglomerated psyllium husk is then passed through a 10 mesh screen to break up any loose clumps and remove traces of coarse material that may have formed.

A flavored psyllium-containing drink mix is prepared using 90.88 parts by weight of the agglomerated psyllium husk, 0.83 parts by weight aspartame, 4.33 parts by weight citric acid, 3.86 parts by weight flavoring agent, and 0.10 parts by weight coloring agent.

The agglomerated psyllium husk, and the flavored agglomerated psyllium husk-containing drink mix, are readily mixable and dispersible in water. Ingestion of a liquid drink prepared by mixing one teaspoon of the drink mix in 8 ounces of water is effective for providing laxative benefits.

A readily dispersible and suspendable agglomerated psyllium husk product is also prepared by passing the agglomerated psyllium husk through a 40 mesh screen. The overs are reduced in size by passing through a Comitrol Processor Model 1700 (sold by Urschel Laboratories Incorporated; Valparaiso, Ind.), and the resulting material is fed back to the 40 mesh screening operation on a continuous basis. 100% of the agglomerated psyllium husk is thereby made to pass through 40 mesh screen, and about 30% of the agglomerated psyllium husk has particle size less than about 120 mesh screen. This agglomerated psyllium husk is then used in the drink mix as described hereinbefore.

What is claimed is:

1. Agglomerated psyllium husk comprising:
   (a) from about 25% to about 99% psyllium husk;
   (b) from about 0.5% to about 20% of maltodextrin coating on said psyllium husk; and
   (c) from about 0.5% to about 20% of citric acid uniformly dispersed throughout the maltodextrin coating on said psyllium husk,
   and wherein further said agglomerated psyllium husk comprises less than about 20% sugar.

2. Agglomerated psyllium husk according to claim 1 wherein the ratio of maltodextrin coating to citric acid uniformly dispersed throughout the maltodextrin coating is within the range of from about 1:10 to about 10:1.

3. Agglomerated psyllium husk according to claim 2 wherein the maltodextrin has a D.E. within the range of from about 5 to about 20.

4. Maltodextrin-coated agglomerated psyllium husk comprising:
   (a) from about 25% to about 98% psyllium husk of particle size such that more than about 90% of the psyllium husk passes through about 40 mesh screen;
   (b) at least about 1% maltodextrin coating on said psyllium husk; and
   (c) at least about 1% citric acid uniformly dispersed throughout the maltodextrin coating on said psyllium husk;
   and wherein further said agglomerated psyllium husk comprises less than about 20% sugar.

5. Maltodextrin-coated agglomerated psyllium husk according to claim 4 wherein the particle size of the psyllium husk is such that essentially all passes through 80 mesh screen; and from about 1% to about 5% citric acid is uniformly dispersed throughout the maltodextrin coating.

6. Agglomerated psyllium husk comprising:
   (a) from about 50% to about 98% psyllium husk of particle size smaller than about 80 mesh screen;
   (b) from about 0.5% to about 75% maltodextrin agglomerating material; and
   (c) from about 1% to about 10% uniformly dispersed citric acid coating on said psyllium husk, wherein said uniformly dispersed citric acid coating is applied to the psyllium husk by spraying with a solution comprising citric acid; and wherein further said agglomerated psyllium husk comprises less than about 20% sugar.

* * * * *